(12) United States Patent
Scopton

(10) Patent No.: US 7,178,520 B2
(45) Date of Patent: *Feb. 20, 2007

(54) MOUTHGUARD HAVING DEVICE SECURING TAB

(75) Inventor: Paul Scopton, Winchester, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/035,785

(22) Filed: Jan. 13, 2005

(65) Prior Publication Data

US 2005/0121028 A1    Jun. 9, 2005

Related U.S. Application Data

(63) Continuation of application No. 10/217,266, filed on Aug. 8, 2002, now Pat. No. 6,851,424.

(51) Int. Cl.
A61M 16/00 (2006.01)
A61C 5/14 (2006.01)

(52) U.S. Cl. ................ 128/200.26; 128/859

(58) Field of Classification Search ........ 128/859–862, 128/200.26, 206.29, 207.14, 207.15, 207.17, 128/DIG. 26; 606/108; 600/237–240; 604/171, 179, 264, 270; 602/902
See application file for complete search history.

(56) References Cited

U.S. PATENT DOCUMENTS

| | | | |
|---|---|---|---|
| 4,185,639 A | | 1/1980 | Linder |
| 5,009,227 A | | 4/1991 | Nieuwstad |
| 5,174,284 A | | 12/1992 | Jackson |
| 5,590,643 A | | 1/1997 | Flam |
| 5,806,516 A | | 9/1998 | Beattie |
| 5,829,430 A | * | 11/1998 | Islava ............. 128/200.26 |
| 6,067,985 A | * | 5/2000 | Islava ............. 128/207.17 |
| 6,096,009 A | | 8/2000 | Windheuser et al. |
| 6,257,238 B1 | | 7/2001 | Meah |
| 6,318,371 B1 | | 11/2001 | Tyszkiewicz |
| 6,408,850 B1 | | 6/2002 | Sudge |
| 6,474,332 B2 | | 11/2002 | Ardnt |
| 6,517,549 B1 | | 2/2003 | Dennis |
| 6,533,761 B2 | | 3/2003 | Bertoch et al. |
| 6,634,359 B1 | | 10/2003 | Rudy, Jr. et al. |

(Continued)

FOREIGN PATENT DOCUMENTS

WO    WO 01/91838    5/2001

(Continued)

OTHER PUBLICATIONS

E-Z-EM, Inc., <http://www.ezem.com/gastroenterology/ezguard.asp?action=gastroenterology>, (accessed Nov. 6, 2002), 2 pages.

(Continued)

*Primary Examiner*—Teena Mitchell
(74) *Attorney, Agent, or Firm*—Christensen O'Connor Johnson Kindness PLLC

(57) ABSTRACT

A mouthguard for allowing medical instruments to be passed into a patient includes an integrally formed or removable locking device. The locking device includes one or more mechanisms for preventing the movement of a guidewire or other medical devices during a surgical procedure.

10 Claims, 2 Drawing Sheets

U.S. PATENT DOCUMENTS

| | | |
|---|---|---|
| 6,655,960 B2 | 12/2003 | Fischer |
| 6,755,191 B2 * | 6/2004 | Bertoch et al. ........ 128/200.26 |
| 6,851,424 B2 * | 2/2005 | Scopton ................. 128/200.26 |
| 2002/0162555 A1 | 11/2002 | West et al. |
| 2005/0090835 A1 * | 4/2005 | Deal et al. ................. 606/108 |

FOREIGN PATENT DOCUMENTS

| | | |
|---|---|---|
| WO | WO 01/62325 A1 | 8/2001 |
| WO | WO 02/076541 A1 | 10/2002 |

OTHER PUBLICATIONS

US Endoscopy, <http://www.usendoscopy.com/biteb.htm>, (accessed Nov. 6, 2002), 2 pages.

<http://www.endoscopepartsplus.com/SABB942.gif>, (accessed Apr. 15, 2003), 1 page.

* cited by examiner

MOUTHGUARD HAVING DEVICE SECURING TAB

CROSS-REFERENCE TO RELATED APPLICATION

The present application is a continuation of U.S. patent application Ser. No. 10/217,266, filed Aug. 8, 2002, now U.S. Pat. No. 6,851,424 the benefit of which are claimed under 35 U.S.C. § 120 and are herein incorporated by reference.

FIELD OF THE INVENTION

The present invention relates to medical devices and in particular to minimally invasive medical devices.

BACKGROUND OF THE INVENTION

As an alternative to conventional surgical techniques, many new minimally invasive techniques are being developed to access and treat internal body tissue. These minimally invasive techniques are generally less traumatic to the patient and heal faster than conventional surgeries.

In many minimally invasive surgical procedures, it is necessary for an endoscopist to route a guidewire from a position outside the patient's body to the position of the tissue to be treated. With the guidewire in place, catheters or devices can be advanced over the guidewire in order to position them adjacent the tissue in question.

For example, in treating the digestive tract, an endoscope is first routed through a patient's alimentary canal and a guidewire is then routed through a lumen in the endoscope in order to position it near the tissue in question. The endoscope is then removed over the guidewire thereby leaving the guidewire at the desired location. Other devices or catheters can then be routed over the guidewire in order to perform a treatment operation. Typically, the proximal end of the guidewire extends out the patient's mouth.

In order to avoid having to reposition the guidewire, it is important that the guidewire not be moved during the surgical procedure.

SUMMARY OF THE INVENTION

To aid in securing the position of a guidewire or other medical device that extends out of a patient's mouth during a medical procedure, the present invention is a mouthguard having a tube through which medical devices may be passed. A flange on the tube prevents the mouthguard from being swallowed, and a locking device is either integrally formed or removably secured to the mouthguard. The locking device has mechanisms for securing one or more of the medical devices in position during a medical procedure.

In one embodiment of the invention, the locking device comprises a tab having a slot into which a guidewire or other medical device can be held with a friction fit. Alternatively, the mechanisms can comprise clips, tabs, hook and loop tape or other mechanisms that prevent a guidewire or other device from being moved during surgery.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENTS

Figure 1:
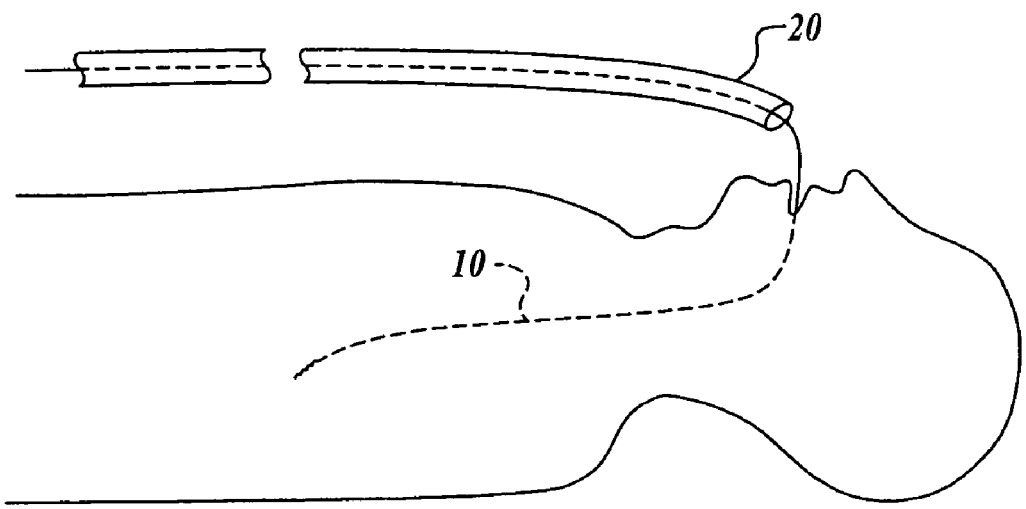
FIG. 1 illustrates a patient undergoing a catheter-based surgical procedure with a conventional catheter and guidewire.
Figure 2:
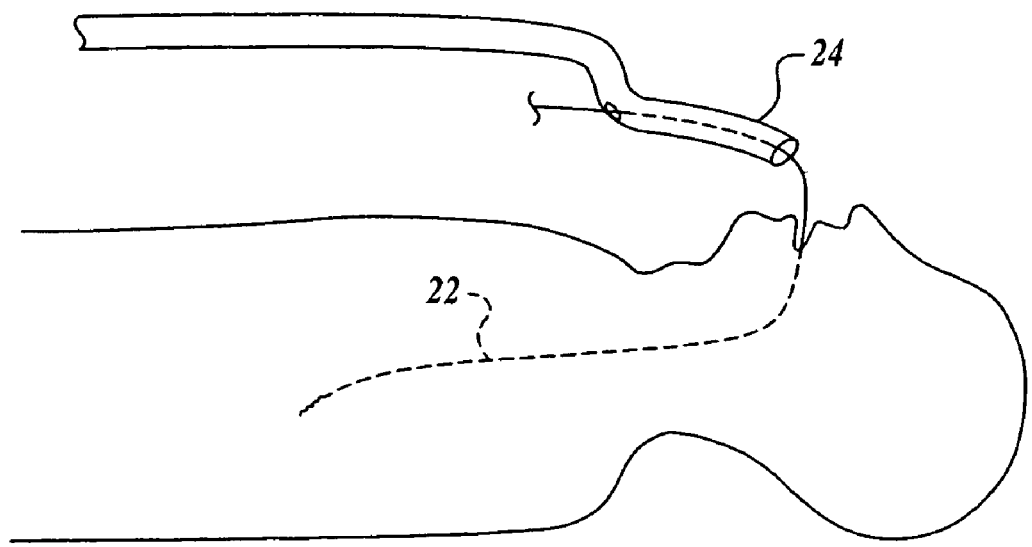
FIG. 2 illustrates a patient undergoing a catheter-based surgical procedure using a rapid exchange-type catheter.

FIGS. 1 and 2 illustrate a patient undergoing a minimally invasive surgical procedure that uses a guidewire. In FIG. 1, a guidewire 10 is positioned with its distal tip adjacent a tissue area to be treated within the patient's body. Typically, the guidewire 10 is routed through a lumen in an endoscope (not shown) such that the physician can see where the guidewire is to be placed. Once the guidewire is in the appropriate location, the physician removes the endoscope over the guidewire, thereby leaving the guidewire with its distal tip at the desired location. With the guidewire in the appropriate position, a catheter 20 can be routed over the guidewire in order to deliver a surgical device or treatment to the tissue in question. Such surgical devices can include balloons, stents, electro- or laser tissue cutting devices, aspirators or therapeutic delivery mechanisms, etc.

If the catheter 20 is a conventional type, it contains a lumen along it entire length through which the proximal end of the guidewire 10 is routed. In order to advance the catheter 20 into the patient, the guidewire 10 must have a length that is at least as long as the catheter 20 such that the physician can grasp the proximal end of the guidewire while advancing the catheter 20 into the patient. With this arrangement, it will be appreciated that the length of the guidewire that extends out of the patient may interfere with the physician's movements and make it more likely that the guidewire may be moved or dislodged and will have to be repositioned.

FIG. 2 shows a patient undergoing a minimally invasive surgical procedure using a "rapid exchange" type catheter that is fitted over a guidewire. In this embodiment, a guidewire 22 is positioned in the patient with its distal tip at a region of interest. Again, the guidewire is most often routed through a lumen in an endoscope to the desired position. The endoscope is then removed over the guidewire leaving the guidewire in place. A catheter 24 is then routed over the guidewire 22. A rapid exchange catheter has a guidewire lumen extends only along a portion of the length of the catheter. To route the catheter 24 over the catheter, the guidewire 22 is inserted through the shorter lumen and the proximal end of the guidewire 22 held securely in order to advance the catheter 24 into the patient. The advantage of the rapid exchange type catheter 24 is that the length of the guidewire 22 can be made significantly shorter than the type required for use with conventional catheters.

Regardless of what type of catheter is used, it is important that the position of the guidewire remain substantially fixed as the physician is operating on the patient.

Figure 3:
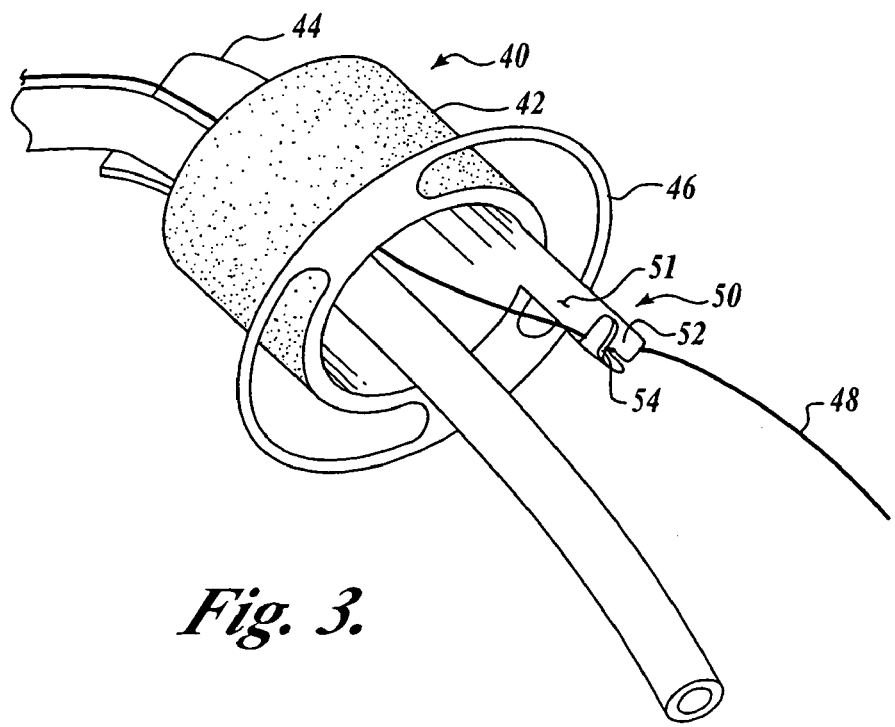
FIG. 3 illustrates a mouthguard having a locking device in accordance with one embodiment of the present invention.

FIG. 3 illustrates one embodiment of the present invention which is used to secure the position of a guidewire or other medical device that is inserted into the patient. A mouthguard 40 has a tube 42 that is positioned in the patient's mouth to provide access into the patient's alimentary or bronchial canals. The mouthguard may include a curved tongue 44 that extends distally from the tube 42 and operates to aid the passage of a catheter or endoscope into the patient's esophagus or trachea. In some embodiments, the outer surface of the tube 42 may be covered with a foam or other compressible material to protect the patient's teeth as surgical devices are inserted into the patient. Alternatively, the tube itself may be formed of a relatively soft material. A flange 46 is positioned at the proximal end of the tube 42 and has a diameter larger than the patient's mouth such that the mouthguard 40 cannot be accidentally swallowed by the patient.

To secure the position of a guidewire positioned in a patient, the mouthguard 40 includes a locking device 50 that is integrally formed with the mouthguard 40. The locking device 50 comprises a tab 51 that extends proximally from the opening of the tube 42. The tab 51 includes a slot 52 having a diameter that narrows to a width that is smaller than the diameter of the guidewire. The guidewire 48 can be secured in the slot 52 with a friction fit. Additionally, the locking device may include a tab 54 under which the guidewire can be passed in order to further secure the guidewire 48 to the locking device 50. The locking device 50 is not limited to securing guidewires but may contain other tabs or slots for securing the position of catheters or other medical devices placed into the patient's body. Other locking mechanisms may include clips, slots, hook and loop-type fasteners, or other mechanisms for securing the position of a medical device to the locking device.

Figure 4:
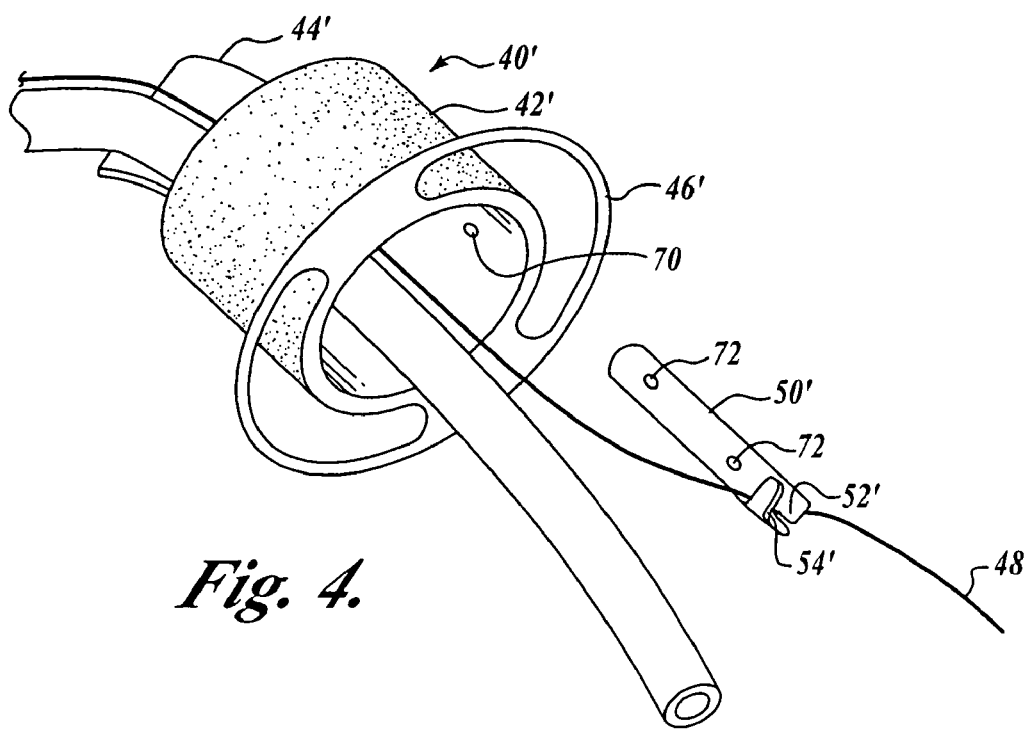
FIG. 4 illustrates a mouthguard having a locking device according to a second embodiment of the present invention.

FIG. 4 shows another embodiment of the mouthguard according to the present invention. A mouthguard 40' includes a tube 42' preferably covered with a compressible material such as foam. Extending from the distal end of the tube 42' is a curved tongue 44'. A flange 46' has a diameter that is larger than the patient's mouth and extends outwardly from the proximal end of the tube 42' such that the mouthguard 40' cannot be swallowed by a patient.

In this embodiment, the mouthguard includes a locking device 50' that is removably secured to the tube 42'. The locking device 50' has a slot 52' into which a guidewire 48 can be secured. In addition, the locking device may include a tab 54' under which the guidewire 48 may be passed in order to secure it to the locking device. The locking device 50' may include other mechanisms for securing the position of a number of medical devices passed through the mouthguard as indicated above. These other mechanisms may be in addition to or in lieu of the slot 52'.

In one embodiment of the invention, the locking device 50' is secured to the mouthguard using tabs positioned on the tube 42' and corresponding holes or slots positioned on the locking device 50' or vice versa. Alternatively, the locking device 50' could be secured to the mouthguard 40' using screws, interlocking channels, clips or other mechanisms for removably securing the two devices together.

While the preferred embodiment of the invention has been illustrated and described, it will be appreciated that various changes can be made therein without departing from the scope of the invention. The scope of the invention is therefore to be determined from the following claims and equivalents thereof.

The embodiments of the invention in which an exclusive property or privilege is claimed are defined as follows:

1. A medical procedure utilizing a guidewire in a patient, comprising:
   positioning a mouthguard in a patient's mouth to provide access into the patient the mouthguard comprising:
   a tube that is insertable into a patient's mouth and through which a guidewire may be passed;
   a flange extending outwardly from the tube, the flange having an outer diameter that is larger than the patient's mouth to prevent the mouthguard from being swallowed; and
   a tab extending from the tube including a locking mechanism for selectively engaging a guidewire passed through the tube;
   advancing a distal end of the guidewire through the mouthguard to a desired location in the patient; and
   securing a proximal end of the guidewire to the locking mechanism of the mouthguard.

2. The medical procedure of claim 1, wherein the proximal end of the guidewire is secured to the locking mechanism by inserting the guidewire into a slot with a friction fit.

3. The medical procedure of claim 1, wherein the proximal end of the guidewire is secured to the locking mechanism by passing the guidewire under a tab to pinch the guidewire.

4. The medical procedure of claim 1, further comprising disengaging the proximal end of the guidewire from the locking mechanism and routing a medical device over the guidewire in order to guide the medical device into the patient.

5. The medical procedure of claim 4, wherein the medical device is a rapid exchange type catheter.

6. A mouthguard, comprising:
   a tube that is insertable into a patient's mouth and through which a guidewire may be passed;
   a flange extending outwardly from the tube, the flange having an outer diameter that is larger than the patient's mouth to prevent the mouthguard from being swallowed; and
   a tab extending from the tube including a locking mechanism for selectively securing a guidewire passed through the tube.

7. The mouthguard of claim 6, wherein the locking mechanism comprises a slot with a width smaller than the diameter of the guidewire.

8. The mouthguard of claim 6, wherein the locking mechanism includes a tab under which the guidewire may be passed to pinch the guidewire.

9. The mouthguard of claim 6, wherein the locking mechanism is integrally farmed with the mouthguard.

10. The mouthguard of claim 6, wherein the locking mechanism is removably secured to the mouthguard.

* * * * *

UNITED STATES PATENT AND TRADEMARK OFFICE
CERTIFICATE OF CORRECTION

PATENT NO. : 7,178,520 B2  Page 1 of 1
APPLICATION NO. : 11/035785
DATED : February 20, 2007
INVENTOR(S) : P. Scopton It is certified that error appears in the above-identified patent and that said Letters Patent is hereby corrected as shown below:

| COLUMN | LINE | ERROR |
|---|---|---|
| 4 | 9 | "patient the" should read --patient, the-- |
| 4 | 15 | "lowcd; and" should read --lowered;-- |
| 4 | 54 | "farmed" should read --formed-- |

Signed and Sealed this

Seventh Day of August, 2007

JON W. DUDAS
*Director of the United States Patent and Trademark Office*